US010739335B2

(12) United States Patent
Harel

(10) Patent No.: US 10,739,335 B2
(45) Date of Patent: Aug. 11, 2020

(54) PROGNOSTIC AND DIAGNOSTIC GLYCAN-BASED BIOMARKERS OF BRAIN DAMAGE

(71) Applicant: MEDICORTEX FINLAND OY, Turku (FI)

(72) Inventor: Adrian Harel, Turku (FI)

(73) Assignee: MEDICORTEX FINLAND OY, Turku (FI)

( * ) Notice: Subject to any disclaimer, the term of this patent is extended or adjusted under 35 U.S.C. 154(b) by 0 days.

(21) Appl. No.: 15/565,753

(22) PCT Filed: Apr. 14, 2016

(86) PCT No.: PCT/FI2016/050246
§ 371 (c)(1),
(2) Date: Oct. 11, 2017

(87) PCT Pub. No.: WO2016/166419
PCT Pub. Date: Oct. 20, 2016

(65) Prior Publication Data

US 2018/0120305 A1 May 3, 2018

(30) Foreign Application Priority Data

Apr. 15, 2015 (FI) ..................................... 20155280

(51) Int. Cl.

| | |
|---|---|
| ***A61K 38/00*** | (2006.01) |
| ***C12Q 1/68*** | (2018.01) |
| ***G01N 33/567*** | (2006.01) |
| ***G01N 33/53*** | (2006.01) |
| ***G01N 33/68*** | (2006.01) |

(52) U.S. Cl.
CPC ..... *G01N 33/5308* (2013.01); *G01N 33/6896* (2013.01); *G01N 2400/12* (2013.01); *G01N 2400/38* (2013.01); *G01N 2800/28* (2013.01)

(58) Field of Classification Search
None
See application file for complete search history.

(56) References Cited

U.S. PATENT DOCUMENTS

| | | | |
|---|---|---|---|
| 5,225,352 | A | 7/1993 | Zanetta et al. |
| 2008/0220013 | A1 | 9/2008 | Hochstrasser et al. |
| 2011/0065197 | A1 | 3/2011 | Urakami et al. |

FOREIGN PATENT DOCUMENTS

| | | | |
|---|---|---|---|
| EP | 1901066 | A1 | 3/2008 |
| WO | WO-2005/015240 | A1 | 2/2005 |
| WO | WO-2005/069852 | A2 | 8/2005 |
| WO | WO-2006/113245 | A2 | 10/2006 |
| WO | WO-2014/133428 | A1 | 9/2014 |
| WO | WO-2015/009907 | A1 | 1/2015 |
| WO | WO-2015/130956 | A2 | 9/2015 |

OTHER PUBLICATIONS

Cummings et al. Essentials of Glycobiology, 2009, 2nd edition, Cold Spring Harbor Lab. Press, Chapter 45.*
Nagaraj et al., Nanomedicine, 2010, 5(3): 369-78.*
Haab, Proteomics Clin. Appl., 2012, 6:346-50.*
Beni-Adani et al., A peptide derived from activity-dependent neuroprotective protein (ADNP) ameliorates injury response in closed head injury in mice, J. Pharmacol. Exp. Ther., 296(1):57-63 (2001).
Bilgen, A new device for experimental modeling of central nervous system injuries, Neurorehabil. Neural Repair, 19(3):219-26 (2005).
Finnish Patent Application No. 20155280, Search Report and First Office Action, dated Dec. 15, 2015.
International Application No. PCT/FI2016/050246, International Preliminary Report on Patentability, dated Oct. 17, 2017.
International Application No. PCT/FI2016/050246, International Search Report and Written Opinion, dated Jul. 7, 2016.
Levine, Increased expression of the NG2 chondroitin-sulfate proteoglycan after brain injury, J. Neurosci., 14(8):4716-30 (1994).
Otto et al., N-glycan structures and N-glycosylation sites of mouse soluble intercellular adhesion molecule-1 revealed by MALDI-TOF and FTICR mass spectrometry, Glycobiology, 16(11):1033-44 (2006).
Yatsiv et al., Erythropoietin is neuroprotective, improves functional recovery, and reduces neuronal apoptosis and inflammation in a rodent model of experimental closed head injury, FASEB J., 19(12):1701-3 (2005).
European Patent Application No. 16721191.1, Communication Pursuant to Article 94(3) EPC, dated Nov. 20, 2018.
Gupta, et al., "Lectin Microarrays for Glycomic Analysis", OMICS A Journal of Integrative Biology, vol. 14, No. 4, pp. 419-436 (2010).
Canadian Office Action dated Sep. 25, 2019, issued in related CA Appl. No. 2,982,503 (9 pages).

* cited by examiner

*Primary Examiner* — Olga N Chernyshev
(74) *Attorney, Agent, or Firm* — Marshall, Gerstein & Borun LLP

(57) ABSTRACT

The present disclosure relates to glycan-based biomarkers for the diagnosis or prognosis of brain damage, such as traumatic brain injury (TBI).

8 Claims, 3 Drawing Sheets

PROGNOSTIC AND DIAGNOSTIC GLYCAN-BASED BIOMARKERS OF BRAIN DAMAGE

FIELD OF THE INVENTION

The present disclosure relates to glycan-based biomarkers for the diagnosis and prognosis of brain damage, such as traumatic brain injury (TBI), subclinical brain injury (SCI) and acquired brain injury (ABI). The glycan-based biomarker protocol may also be used as an end point in clinical trials. More specifically, the biomarkers of the present invention can be used in diagnostic tests to determine, qualify, and/or assess brain injury status, for example, to diagnose brain injury, in an individual, subject or patient. In particular embodiments, brain injury status can include determining a subject's subclinical brain injury status or SCI status, for example, to diagnose SCI, in an individual, subject or patient (conscious or not).

BACKGROUND OF THE INVENTION

Brain injuries are complex and can have multiple severe clinical outcomes. Traumatic brain injury (TBI) is the leading cause of central nervous system impairment in these days. More than 1.7 million individuals suffer annually from TBI in the US alone. According to the CDC, the highest incidence of TBI occurs among children 0-4 years old, adolescents 15-19 years old, and adults over 65 years of age. Despite the broad range of the population affected, TBI is still under-served and remains an unexplored pathological condition.

Each year, 35,000 persons in Finland suffer a TBI, 1150 of whom die and 10,000 are left with a permanent impairment. The annual costs of TBI amount to € two billion. The annual figures at the European level are 2.5 million new cases, 75,000 deaths, 400,000 permanent impairments. TBI causes more deaths in the age-group <35 years than all diseases put together, but it affects all age groups. This would imply that worldwide there are over 16.5 million serious TBI's every year.

Traditionally, TBI has been acutely diagnosed and classified by neurological examinations, such as Glasgow Coma Scale (GCS). However, the use of the GCS as a diagnostic tool is subject to a number of important limitations. Recent research has provided evidence that the use of sedative drugs precluded accurate GCS assessment during the first 24 h. Further challenges to diagnosis are presented by the evolving nature of some brain lesions, which can lead to further neurological impairment. In addition, neurological responses after TBI can vary over time for reasons unrelated to the injury. Still further challenges include the trauma subject's possible unconsciousness or inability to communicate.

Neuroimaging techniques, such as x-ray, CT scanning and MRI, are used to provide information on injury magnitude and location, and are not influenced by the aforementioned disadvantages. However, CT scanning has low sensitivity to diffuse brain damage, and availability and utility of MRI is limited. MRI is also very impractical to perform if subjects are physiologically unstable, and can lead to inaccurate diagnoses in military injuries in which metal fragments are common.

Moreover, mild and moderate TBI represent more than 90% of TBI injuries; this injury range represents the greatest challenges to accurate acute diagnosis and outcome prediction. Unlike severe TBI, there is no universally recognized neurologic assessment scale such as the GCS, and many cases of mild TBI are classified as subclinical brain injury (SCI). The widespread recognition of inadequate approaches to diagnose mild TBI suggests the need for significant improvement in the diagnosis and classification of TBI, such as the use of biomarkers to supplement functional and imaging-based assessments. These biomarkers can be altered gene expression, protein or lipid metabolites, or a combination of these changes after traumatic brain injury, reflecting the initial insult (the primary injury) and the evolution of a cascade of secondary damage (the secondary injury). In particular, subclinical brain injury status or SCI could be diagnosed with a biomarker analysis.

As with many injuries, increased serum levels of cytokines and chemokines have been noted post-TBI and, as such, have been proposed as potential surrogate markers for TBI outcome. However, to date, there are no approved biomarkers for the diagnosis or prognosis of TBI. This is because of several obstacles to the development of reliable blood biomarkers of TBI. For instance, the blood-brain barrier (BBB) hinders the assessment of biochemical changes in the brain by use of blood biomarkers in mild TBI, although impaired BBB integrity, as seen in severe TBI, can increase the levels of brain-derived proteins in the blood. Nevertheless, owing to their dilution in the much larger plasma volume, biomarkers that are highly expressed within the central nervous system exist at very low concentrations in blood. Moreover, some potential biomarkers undergo proteolytic degradation in the blood, and their levels might be affected by clearance from blood via the liver or kidney. As a consequence, reliable blood biomarkers have been extremely difficult to identify.

There is thus an identified need for a reliable, simple, and easy-to-use test for brain damage, especially for use in emergency response situations like car accidents and in battlefields.

BRIEF DESCRIPTION OF THE INVENTION

In one aspect, the present invention provides a method of diagnosing, monitoring, or prognosing a brain injury in a subject. The method comprising the steps of: providing a sample of a bodily fluid from said subject; determining the level of at least one glycan-based biomarker in said sample; and providing a diagnosis based on said determined level of said at least one glycan-based biomarker; wherein the diagnosis confirms the presence or absence of brain injury in the subject.

In another aspect, the present invention provides use of at least one glycan-based biomarker for diagnosing, monitoring, or predicting the outcome of a brain injury.

In a further aspect, the present invention provides a kit or a device for use in the present method of diagnosing, monitoring, or prognosing a brain injury in a subject. The kit or device comprises at least one lectin, antibody, or a combination thereof that selectively binds to a glycan-based biomarker, and a control for comparing to a measured value of binding.

Specific embodiments, details, and advantages of different aspects of the invention are set forth in the dependent claims, detailed description and examples.

BRIEF DESCRIPTION OF THE DRAWINGS

In the following, the invention will be described in greater detail by means of preferred embodiments with reference to the attached drawings, in which.

DETAILED DESCRIPTION OF THE INVENTION

Figure 1:
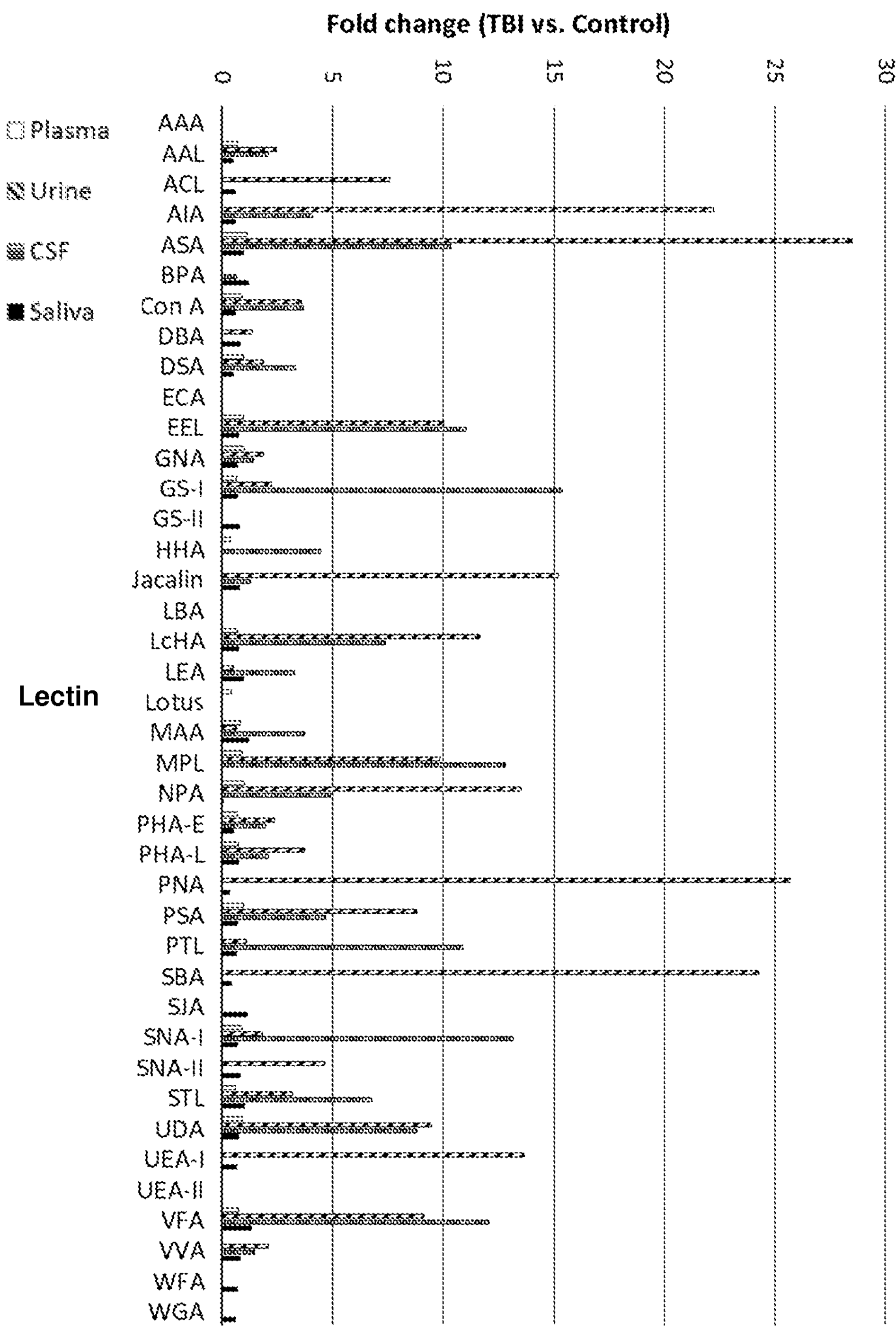
FIG. 1 shows changes in spot fluorescence intensities between TBI rats and control rats in samples of plasma, urine, cerebrospinal fluid (CSF) and saliva.

The present disclosure relates to diagnostic and prognostic glycan-based brain injury biomarkers, which may be used e.g. for identifying subjects with severe TBI/ABI, who are at risk of secondary brain injury and therefore require increased surveillance, or subjects with mild TBI/ABI or subclinical brain injury (SCI), who otherwise may remain undiagnosed and untreated. The present biomarkers may also be applied in cases where there are no external signs of injury or where the injured person, such as a baby or a coma patient, cannot describe the injury. For example, brain injury status includes, without limitation, the presence or absence of brain injury in a subject, the risk of developing brain injury, the stage or severity of brain injury, the progress of brain injury (e.g., progress of brain injury over time) and the effectiveness or response to treatment of brain injury (e.g., clinical follow up and surveillance of brain injury after treatment). Based on this status, further procedures may be indicated, including additional diagnostic tests or therapeutic procedures or regimens.

As used herein, the term "biomarker" refers to a molecule that is detectable in a biological sample obtained from a subject and that is indicative of a brain damage in the subject. Markers of particular interest in the invention include glycan-based biomarkers showing differences in glycosylation between a sample from an individual with a brain damage and a healthy control.

As used herein, the term "glycan-based biomarker" refers to a polysaccharide, i.e. a polymer comprising two or more monosaccharide residues, as well as to a carbohydrate portion of a glycoconjugate, such as a glycoprotein, a glycolipid, a peptidoglycan, or a proteoglycan, or a fragment thereof. Glycan-based biomarkers may comprise either homo-polymeric or heteropolymeric monosaccharide residues, and they may be either linear or branched. As used herein, the terms "glycan", "polysaccharide" and "carbohydrate" are interchangeable, unless otherwise indicated.

Glycocalyx is an extracellular polymeric coating surrounding many prokaryotic and eukaryotic cells consisting of glycoproteins, glycolipids, proteoglycans and glycosaminoglycans. The constituents of the glycocalyx play an important role e.g. in the process of cell signalling, virus transfection, and immunity.

In accordance with the present invention, glycan-based biomarkers include but are not limited to carbohydrates, sugars, glycans, monosaccharides and/or polysaccharides, glycoproteins and glycopolymers. These biomarkers may be present in blood plasma or serum after brain injury, in cerebrospinal fluid (CSF) after brain injury, in lymph fluid after brain injury, in urine after brain injury, in saliva after brain injury, in tears after brain injury or in exudate after brain injury.

The biomarkers are differentially present in unaffected subjects (normal control or non-brain injury) and subjects with brain injury, and, therefore, are useful in aiding in the determination of brain injury status. In certain embodiments, the biomarkers are measured in a sample taken from a subject using the methods described herein and compared, for example, to predefined biomarker levels and correlated to brain injury status. In particular embodiments, the measurement(s) may then be compared with a relevant diagnostic amount(s), cut-off(s), or multivariate model scores that distinguish a positive brain injury status from a negative brain injury status. The diagnostic amount(s) represents a measured amount of a biomarker(s) above which or below which a subject is classified as having a particular brain injury status. For example, if the biomarker(s) is/are up-regulated compared to normal during brain injury, then a measured amount(s) above the diagnostic cut-offs(s) provides a diagnosis of brain injury. Alternatively, if the biomarker(s) is/are down-regulated during brain injury, then a measured amount(s) at or below the diagnostic cut-offs(s) provides a diagnosis of non-brain injury. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from subjects with the different brain injury statuses, and drawing the cut-off to suit the desired levels of specificity and sensitivity.

An advantage of cerebrospinal fluid biomarkers is that the CSF is in direct contact with the extracellular matrix in the brain and, thus, it mirrors biochemical changes in the brain. For these reasons, the CSF might be considered an optimal source of biomarkers of brain injury. However, given that CSF must be obtained by invasive lumbar puncture, availability of biomarkers of brain damage that can be assayed in blood samples would be beneficial. Serum or plasma biomarkers are of special importance in especially blast-induced TBI because they are typically associated with military operations with limited access to imaging and other diagnostic tools of hospitals. The combination of physical damage and psychological effects makes blast-induced TBI especially difficult to diagnose. Thus, plasma and serum biomarkers that can distinguish between the physical and psychological components of the injury would be of special value.

As used herein, the term "brain damage" refers to the destruction or degeneration of brain cells due to one or more internal or external factors. Non-limiting examples of brain damage include traumatic brain injury (TBI), acquired brain injury (ABI), subclinical brain injury (SCI) and neurodegenerative conditions. Non-limiting examples of typical neurodegenerative conditions include Huntington's disease, Parkinson's disease, Alzheimer's disease and Chronic Traumatic Encephalopathy. As used herein, the terms "brain damage" and "brain injury" are interchangeable, unless otherwise indicated.

As used herein, the term "traumatic brain injury" (TBI) refers to brain injury caused by external physical trauma. Non-limiting examples of incidences resulting in TBI include falls, vehicle collisions, sports collisions, and combats. The term includes both mild and severe TBI including closed-head injuries, concussions or contusions and penetrating head injuries.

As used herein, the term "acquired brain injury" (ABI) refers to a brain damage not caused by an external brain injury or a hereditary condition. ABI may occur after birth as a result of complications, a disorder or congenital malady, or it may result from, for instance, stroke, surgery, removal of a brain tumour, infection, chemical and/or toxic poisoning, hypoxia, ischemia, substance abuse, or a combination thereof.

The term "brain injury" also refers to subclinical brain injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness and/or medications, particularly sedation and anaesthesia.

As used herein, the term "subject" refers to any mammal, including animals and human subjects. Animals include, but are not limited to, pets, farm animals, working animals, sporting animals, show animals, and zoo animals. Non-limiting examples of typical human subjects suffering from or pre-disposed to brain damage, TBI in particular, include babies, children and young adults, particularly male; elderly; athletes, particularly boxers, ice-hockey players, soccer players, and skateboarders; and soldiers. The terms "human subject" and "individual" are interchangeable. Typically, the subject is known to have or suspected of having a brain injury, such as TBI or ABI.

As used herein, the term "diagnosis" refers to the determination of whether or not a subject has a brain damage, such as TBI or ABI. The term is also meant to include instances where the presence of a brain damage is not finally determined but that further diagnostic testing is warranted. In such embodiments, the method is not by itself determinative of the presence or absence of a brain damage in the subject but can indicate that further diagnostic testing is needed or would be beneficial. The methods, therefore, can be combined with one or more other diagnostic methods for the final determination of the presence or absence of a brain damage in the subject. Examples of such other diagnostic methods include, but are not limited to, CT and MRI, and are well known to a person skilled in the art. As used herein, a "final determination" or "final diagnosis" refers to ascertaining the presence or absence of a brain damage in a subject. The final determination or final diagnosis can be the result of any of the methods of the invention which, in some embodiments, can include more than one diagnostic test.

As used herein, the term "comparing" refers to making an assessment of how the proportion, level or cellular localization of one or more biomarkers in a sample from a subject relates to the proportion, level or localization of the corresponding one or more biomarkers in a standard or control sample. For example, "comparing" may refer to assessing whether the proportion, level, or cellular localization of one or more biomarkers in a sample from a subject is the same as, more or less than, or different from the proportion, level, or localization of the corresponding one or more biomarkers in standard or control sample. More specifically, the term may refer to assessing whether the proportion, level, or cellular localization of one or more biomarkers in a sample from a subject is the same as, more or less than, different from or otherwise corresponds (or not) to the proportion, level, or cellular localization of predefined biomarker levels that correspond to, for example, a subject having subclinical brain injury (SCI), not having SCI, is responding to treatment for SCI, is not responding to treatment for SCI, is/is not likely to respond to a particular SCI treatment, or having/not having another disease or condition. In a specific embodiment, the term "comparing" refers to assessing whether the level of one or more biomarkers of the present invention in a sample from a subject is the same as, more or less than, different from other otherwise correspond (or not) to levels of the same biomarkers in a control sample (e.g., predefined levels that correlate to uninfected individuals, standard SCI levels, etc.).

The present biomarkers and methods may be used not only for diagnostic purposes but also for prognosis or predicting the outcome of the brain damage, or monitoring the subject's survival from the brain damage or response to treatment.

The present biomarkers and methods may be used as a clinical end point in clinical trials for treating TBI or ABI, providing the outcome of the brain damage, or monitoring the subject's survival from the brain damage or response to treatment.

In some embodiments of the present invention, the diagnosis or prognosis of a brain damage may comprise determination of the presence or absence of one or more of the present glycan-based biomarkers in a biological sample obtained from a subject whose possible brain damage is to be determined. Multiplexed assays can provide substantially improved diagnostic precision. In a specific embodiment, the present invention provides methods for determining the risk of developing brain injury in a subject. Biomarker percentages, amounts or patterns are characteristic of various risk states, e.g., high, medium or low. The risk of developing brain injury is determined by measuring the relevant biomarkers and then either submitting them to a classification algorithm or comparing them with a reference amount, i.e., a predefined level or pattern of biomarkers that is associated with the particular risk level.

In another embodiment, the present invention provides methods for determining the severity of brain injury in a subject. Each grade or stage of brain injury likely has a characteristic level of a biomarker or relative levels of a set of biomarkers (a pattern). The severity of brain injury is determined by measuring the relevant biomarkers and then either submitting them to a classification algorithm or comparing them with a reference amount, i.e., a predefined level or pattern of biomarkers that is associated with the particular stage.

In some other embodiments of the present method, the diagnosis or prognosis of a brain damage may comprise determination of the amount of one or more glycan-based biomarkers, or the relative amounts thereof as compared to, for example, the amount of each other, one or more other glycan, and/or a known standard. In some embodiments, diagnosis or prognosis of brain damage may be based on relative ratios of glycan-based biomarkers in different body fluids, such as a blood/CSF ratio.

In some further embodiments, the amounts or relative ratios of one or more glycan-based biomarker may be compared to a predetermined threshold value which is indicative of the presence or absence of a brain damage or is useful in assessing the progression or regression of the brain damage. Such a comparison to a threshold value may result in a final or non-final diagnosis or a determination in regard to the progression or regression of the brain damage. Statistical methods for determining appropriate threshold values will be readily apparent to those of ordinary skill in the art. The threshold values may have been determined, if necessary, from samples of subjects of the same age, race, gender and/or disease status, etc. The threshold value may originate from a single individual not affected by a brain damage or be a value pooled from more than one such individual.

In some preferred embodiments, glycan-based biomarkers may also be detected and/or quantified with the use of lectins. Lectins are a well-known family of carbohydrate-binding proteins, i.e. macromolecules that are highly specific for given glycans on the basis of their sugar moiety structures and sequences. Lectins can be classified into distinct groups according to their carbohydrate specificity including, but not limited to, fucose-specific, mannose specific, N-acetylglucosamine-specific, and galactose/N-acetylglucosamine-specific lectins. For instance, FIGS. 1 to 3 disclose which lectins are particularly suitable for distinguishing subjects with TBI from those not having TBI. As indicated, different sample types may exhibit different profiles of lectin-binding glycan biomarkers. Accordingly, lectins capable of identifying subjects with brain injury may be used in either individually or in any combination thereof.

In some further embodiments, glycan-based biomarkers may also be detected and/or quantified with the use of galectins, the most widely expressed class of lectins in all organisms. Galectins are a family of proteins defined by their binding specificity for β-galactoside sugars, such as N-acetyllactosamine (Galβ1-3GlcNAc or Galβ1-4GlcNAc), which can be bound to proteins by either N-linked or O-linked glycosylation. They are also termed S-type lectins due to their dependency on disulphide bonds for stability and carbohydrate binding. Among 15 galectins discovered in mammals, only galectin-1, -2, -3, -4, -7, -8, -9, -10, -12 and -13 have been identified in humans, to date. As used herein, "galectins" are encompassed by the term "lectins", unless otherwise indicated.

Standard techniques of protein microarray technology can be applied to analyse the glycan-based biomarkers. In such microarrays, lectins are immobilized on a solid support, such as a slide, in a high spatial density. Each lectin may be arrayed at several concentrations and in replicates on each slide. The concentration ranges may be tailored for each of the lectins and calibrated to provide a linear response within the same range, regardless of the affinity of the lectin. A sample of intact glycan-based biomarkers is applied to the array, and its binding pattern is detected by a label, such as a fluorescent label, a radioactive label, or a chemiluminescent label, which is placed either on the biomarker itself or on the lectin directed toward the carbohydrate moieties of the biomarker. Streptavidin may be used for detecting biotinylated samples. Also, sandwich based methods which utilize antibody detection may be employed, as is apparent to those with ordinary skill in the art.

Suitable microarray substrates include, but are not limited to, glass, silica, aluminosilicates, borosilicates, metal oxides such as alumina and nickel oxide, gold, various clays, nitrocellulose or nylon. In some embodiments a glass substrate is preferred. In other embodiments, the substrate may be coated with a compound to enhance binding of the lectin to the substrate. In some further embodiments, lectins have been arrayed on a nitrocellulose membrane-coated glass slide. In some still further embodiments, one or more control lectins are also attached to the substrate.

In some embodiments, a commercially available lectin array, which encompasses one standard glass slide, which is spotted with 8 wells of identical lectin arrays, may be employed. Each lectin, together with the positive controls is arrayed in duplicate. The slide comes with an 8-well removable gasket which allows for the process of 8 samples using one slide. Four-slide slides can be nested into a tray, which matches a standard microplate and allows for automated robotic high throughput process of 64 arrays simultaneously.

Unlike other conventional methods, e.g., liquid chromatography and mass spectrometry, lectin microarrays enable rapid and high-sensitivity profiling of complex glycan features without the need for liberation of glycans. Target samples include an extensive range of glycoconjugates involved in cells, tissues, body fluids, as well as synthetic glycans and their mimics. Various procedures for rapid differential glycan profiling have been developed for glycan-related biomarkers and are commercially available.

In one embodiment, the present invention provides methods for determining the course of brain injury in a subject. Brain injury course refers to changes in brain injury status over time, including brain injury progression (worsening) and brain injury regression (improvement). Over time, the amount or relative amount (e.g., the pattern) of the biomarkers changes. For example, biomarker "X" may be increased with brain injury, while biomarker "Y" may be decreased with brain injury. Therefore, the trend of these biomarkers, either increased or decreased over time toward brain injury or non-brain injury indicates the course of the condition. Accordingly, this method involves measuring the level of one or more biomarkers in a subject at least two different time points, e.g., a first time and a second time, and comparing the change, if any. The course of brain injury is determined based on these comparisons.

In another embodiment, the present invention provides methods for determining the therapeutic efficacy of a pharmaceutical drug. These methods are useful in performing clinical trials of the drug, as well as monitoring the progress of a subject on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of one or more of the biomarkers of the present invention may change toward a non-brain injury profile. Therefore, one can follow the course of one or more biomarkers in the subject during the course of treatment. Accordingly, this method involves measuring one or more biomarkers in a subject receiving drug therapy, and correlating the biomarker levels with the brain injury status of the subject (e.g., by comparison to predefined levels of the biomarkers that correspond to different brain injury statuses). One embodiment of this method involves determining the levels of one or more biomarkers in minimum at two different time points during a course of drug therapy, e.g., a first time and a second time, and comparing the change in levels of the biomarkers, if any. For example, the levels of one or more biomarkers can be measured before and after drug administration or at two different time points during drug administration. The effect of therapy is determined based on these comparisons. If a treatment is effective, then the one or more biomarkers will trend toward normal, while if treatment is ineffective, the one or more biomarkers will trend toward brain injury indications.

Suitable methods for use in detecting or analysing glycan-based biomarkers include, but are not limited to, Biocore studies, mass spectrometry, electrophoresis, nuclear magnetic resonance (NMR), chromatographic methods or a combination thereof. Specifically, the mass spectrometric method can be, for example, LC-MS, LC-MS/MS, MALDI-MS, MALDI-TOF, TANDEM-MS, FTMS, multiple reaction monitoring (MRM), quantitative MRM, or Label-free binding analysis. Examples of mass spectrometers are time-of-flight, magnetic sector, quadrupole filter, ion trap, ion cyclotron resonance, electrostatic sector analyser, hybrids or combinations of the foregoing, and the like. In yet another embodiment, mass spectrometry can be combined with another appropriate method(s) as may be contemplated by one of ordinary skill in the art. In another embodiment, the mass spectrometric technique is multiple reaction monitoring (MRM) or quantitative MRM. The electrophoretic method can be, for example, capillary electrophoresis (CE) or isoelectric focusing (IEF), and the chromatographic methods can be, for example, HPLC, chromatofocusing, or ion exchange chromatography.

In some embodiments, detecting, measuring and/or analysing glycan-based biomarkers in a sample may be carried out by any appropriate enzyme assay available in the art. Such assays include, but are not limited to, galactose oxidase assays.

In some further embodiments, one or more different kinds of binding assays may be used for detecting, measuring and/or analysing the present glycan-based biomarkers. For instance, a competitive lectin/galectin mode may be employed, wherein a pre-labelled glycan competes with a glycan from a sample to be analysed for a limited number of binding sites offered by the lectin/galectin. Alternatively or in addition, said binding assay may be carried out in a sandwich mode, wherein one lectin/galectin is used to bind a glycan contained in or derived from a sample to be analysed from one side, and another lectin/galectin, conjugated with a detectable label, binds to the other side of the glycan or the glycan-lectin/galectin complex formed.

In still other embodiments, the biomarkers of the present invention can be detected and/or measured by immunoassays, either in a competitive or sandwich mode. Those skilled in the art know how to carry out such immunoassays. Furthermore, antibodies suitable for this purpose are available commercially. Further suitable antibodies may be produced by methods well known in the art.

In some further embodiments, a combination of a lectin/galectin assay and an immunoassay may be employed for detecting, measuring and/or analysing the present biomarkers in a sample taken from a subject. For this purpose, both a capture reagent and a detection reagent are required. Said capture reagent may be a lectin or a galectin, while said detection reagent may be a detectably labelled antibody, or vice versa.

The present invention also contemplates traditional immunoassays including, for example, sandwich immunoassays such as ELISA or fluorescence-based immunoassays, as well as other enzyme immunoassays. In a SELDI-based immunoassay, a bio specific capture reagent for the biomarker is attached to the surface of an MS probe, such as a pre-activated lectin chip array. The biomarker is then specifically captured on the biochip through this reagent, and the captured biomarker is detected by mass spectrometry.

As is readily understood by those skilled in the art, more than one type of lectins/galectins and/or more than one type of antibodies may be used in the binding assays set forth above. In other words, several different lectins/galectins and antibodies may be used in a reaction to enhance the binding affinity or specificity. Furthermore, multiple different reactions may be carried out simultaneously or sequentially for detecting different glycan-based biomarkers in a sample to be analysed.

It is also contemplated that glycans or glycan complexes contained in a sample to be analysed may be immobilized directly to a surface, such as a microplate well, a glass surface (e.g. a slide), a metal surface (e.g. a silver or gold leaf) by opposite charges, by a glue, of by affinity binding, and be subsequently detected, for instance, by a detectably labelled lectin or antibody.

In accordance with the above, molecules suitable for use in detecting glycan-based biomarkers in a sample to be analysed include, but are not limited to, lectins, galectins, antibodies, and competitive small molecules. Said detection molecules may be visualized, or made otherwise measurable, using for instance conjugated colour reagents, labels, or dyes. Enzyme labels suitable for this purpose include those that upon addition of a substrate catalyse a reaction leading to a measurable change in colour, in luminescence, or in production of a precipitate. Non-limiting examples of such enzyme labels include horseradish peroxidase (HRP) and alkaline phosphatase (AP). Photoluminescent lables, including fluorescent dyes (prompt), lanthanide chelates (for time-resolved fluorescence), and photon upconversion labels may be used for detecting said detection molecules. Furthermore, the detection may be based on bioluminescence and chemiluminescence (as e.g. in luciferin-based detection), or on electrochemiluminescence (with e.g. ruthenium complexes). Also biotin and its derivatives, which enable binding and detection by labeled avidin or labeled streptavidin, as well as various radioactive isotopes may be used for the detection. The detection may also be carried out using beads and particles, including, for example, coloured latex particles, coloured synthetic polymer particles, colloidal metals such as gold and silver particles, (para)magnetic beads, and fluorophore-dyed particles.

In several embodiments, the biomarkers of the present invention may be detected by means of an electrochemical-luminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, nonradioactive and offer a choice of convenient coupling chemistries.

Furthermore, a sample may also be analysed by means of a passive or active biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Lectin biochips are biochips adapted for the capture of glycans. Many lectin biochips are described in the art.

The present disclosure also provides kits which can be used to determine the presence or absence of, or to measure the levels of one or more glycan-based biomarker disclosed herein. In one embodiment, the kit comprises a package containing one or more lectins which selectively bind(s) to one or more glycan-based biomarker, and a control for comparing to a measured value of binding. In some embodiments, the control is a threshold value for comparing to the measured value. The kit can also include a detectable label.

The kit for qualifying brain injury status may be provided as an immuno-chromatography strip comprising a membrane on which the antibodies are immobilized, and a means for detecting the biomarker(s). The kit may comprise a plastic plate on which a sample application pad, on which antibody bands and a secondary antibody band are immobilized and an absorbent pad are positioned in a serial manner, so as to keep continuous capillary flow of blood serum.

In certain embodiments, a subject can be diagnosed by adding blood, plasma or serum from the subject to the kit and detecting the relevant biomarkers conjugated with antibodies, specifically, by a method which comprises the steps of: (i) collecting blood, plasma or serum from the subject; (ii) separating blood serum from the subject's blood; (iii) adding the blood plasma or serum from subject to a diagnostic kit; and, (iv) detecting the biomarkers conjugated with antibodies. In this method, the antibodies are brought into contact with the subject's blood. If the biomarkers are present in the sample, the antibodies will bind to the sample, or a portion thereof. In other kit and diagnostic embodiments, blood, plasma or serum need not be collected from the subject (i.e., it is already collected). Moreover, in other embodiments, the sample may comprise a tissue sample or a (non-invasive) clinical sample such as saliva or other body fluids as described herein.

The kit can also comprise a washing solution or instructions for making a washing solution, in which the combination of the capture reagents and the washing solution allows capture of the biomarkers on the solid support or column for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

As is apparent to a skilled person, the present lectin array kit can be used with either a label-based method or as a sandwich-based method. In one embodiment, the label based method is used for biotin samples containing proteoglycans and glycoproteins for direct detection on the array via a Cy3 equivalent dye-conjugated Biotin-Streptavidin complex. In another embodiment, a sandwich-based method is used for antibody detection of glycocalyx elements (glycolipids, glycoproteins, etc.) captured on the array. Labelled reporter antibodies specific for the glycocalyx elements of interest may be provided in the kit or supplied by the user of the kit. An example protocol for this procedure with a general "Antibody Cocktail" may be included in a user manual. In some non-limiting embodiments, specific antibody concentrations and conditions may need to be determined by the end user.

In one embodiment of the biomarker detection kit, HRP protein and fluorescent light may be employed in order to detect the biomarker in a body fluid and to indicate the quantity of the biomarker in percentage. This may be incorporated into a portable application that indicates the severity of brain damage on a scale comprising, but not limited to, none, mild, moderate and severe. In another embodiment, an analogous yes/no reply is received. These examples do not exclude other possible embodiments.

In some embodiments, the present invention provides use of at least one antibody in a kit or in a device to detect brain damage, where the antibody may be a polyclonal or a monoclonal antibody of any species, or a fragment thereof, either enzymatically cleaved or recombinantly produced, or a humanized antibody, and where the antibody recognizes and binds glycan, glycoprotein, peptidoglycan, proteoglycan, glycolipid, protein, small molecule, lectin, or antibody of another species (generally 'antigens'). Said antibody may be used, for instance, as i) a capture reagent, wherein the antibody is immobilized on a solid substrate to bind its antigen from a sample medium;

ii) an antibody that is immobilized on a solid substrate to bind an analyte-specific capture reagent (for example lectin) so that the bound agent (lectin) is able to capture the analyte (glycan) from a sample;

iii) a primary detection reagent, wherein an antibody conjugated to any label (labeled antibody) recognizes and binds directly an antigen;

iv) a secondary detection reagent, wherein a labelled antibody recognizes and binds a primary detection reagent that is bound to the analyte. For example, a labeled antibody binds to a lectin that has bound to its cognate glycan, or a labeled antibody from one species (e.g. goat) that recognizes and binds an antibody of another species (e.g. mouse) which has bound its antigen;

v) an antibody for recognizing and binding a non-glycan part of a glycan-containing molecule. e.g. a glycoprotein, where the glycoprotein or a fragment thereof is first bound to e.g. lectin via its glycan moiety and then is recognized and bound by an antibody that is specific to the peptide part of the molecule; or vi) antibody for use in immunoblotting assays.

The kit may also comprise a combination of antibodies for different purposes.

All embodiments, details, advantages, and the like of the present kit also apply to a device for use in different aspects and embodiments of the present invention. Also, all embodiments, details, advantages, and the like of the present methods apply to the present kit, and vice versa. In particular, one or more compounds, compositions, or reagents disclosed as suitable for carrying out the present methods may be comprised in the present kit. Likewise, anything disclosed with reference to the kit, apply to the present methods as well.

Without further elaboration, it is believed that one skilled in the art, using the preceding description, can utilize the present invention to the fullest extent.

Non-limiting examples of advantages associated with the present glycan-based biomarkers include that they are brain-tissue specific, able to cross the blood-brain barrier into the bloodstream within minutes of injury, and can be detected using a point-of-care blood test or other body fluids. Furthermore, the biomarkers may either increase or decrease following the injury, but nevertheless they are in correlation with the severity of the injury. Preferably, the present biomarkers may correlate with injury magnitude, survivability, and/or neurologic outcome, or they may be indicative of the extent of neuronal and glial cell loss, axonal, and vascular damage. The present biomarkers can significantly add to the current diagnostic palette for brain damage.

EXAMPLES

All animal experiments are carried out according to institutional guidelines that are in compliance with national and international laws for the care and use of laboratory animals, and under approval by national Ethical Committee.

Example 1

A mouse model of experimental closed head injury disclosed by Yatsiv et al. in FASEB J. 2005, 19:1701-1703 is employed for identifying changes, increase or decrease, in the level of glycan-based biomarkers after a head trauma caused by a weight-drop onto an exposed skull.

Severity of the injury is assessed according to the Neurological Severity Score disclosed by Beni-Adani et al. (J. Pharmacol. Exp. Ther. 2001, 296:57-63) on the basis of ten individual tasks reflecting motor function, alertness, and behaviour. Severity assessment is carried out 1 hour and 7 days after the trauma in order to allocate the mice into comparable study groups in order to find a correlation between the severity of damage and level of detected biomarker.

After euthanization, body fluids (including urine, blood plasma or serum, and CSF) from normal and brain injured animals are collected and analysed for glycan-based biomarkers using a lectin assay, and the brains are evaluated histologically.

Example 2

A rat model of experimental closed head injury disclosed by Bilgen et al. (Neurorehabil. Neural Repair, 2005, 19:219-226) with some modifications is employed for identifying changes, increase or decrease, in the level of glycan-based biomarkers after a head trauma.

In vivo T2 weighted magnetic resonance imaging (MRI) is performed on the animals to depict the pathologies, including lesion size, tissue viability, and brain oedema, of the resulting injuries in the corresponding neuronal tissues at 24 h and day 3.

After euthanization, histological evaluation of the injury in the cortex and hippocampus is performed. Additionally, body fluids (including urine, blood plasma or serum, and CSF) from normal and brain injured animals are collected and analysed for glycan-based biomarkers using a lectin assay.

Example 3

A controlled cortical impact was carried out to exposed dura of anesthetized rats according to Bilgen et al. (Neurorehabil. Neural Repair, 2005, 19:219-226) with modifications. The animals were terminated at various times elapsed after the operation. Samples of urine, blood plasma, saliva and cerebrospinal fluid (CSF) were collected and processed using regular methods well known to professionals skilled in the art.

The samples were incubated on a lectin array, and after washing, a fluorescent conjugate was allowed to bind to the captured glycans or glycan-containing complexes. The spots were visualized and the fluorescence intensities were recorded with a laser scanner.

Figure 2:
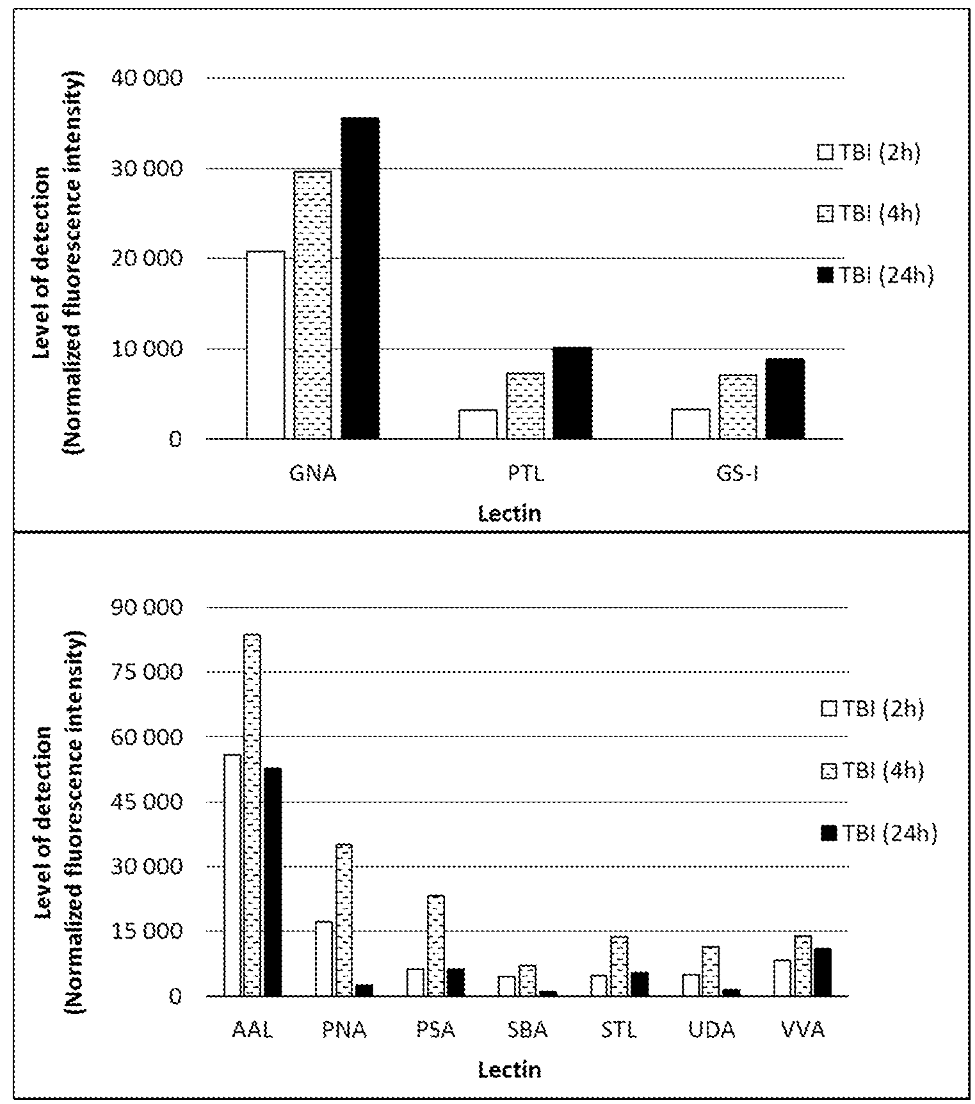
FIG. 2 shows normalized fluorescence intensities of spots of selected lectins contacted with urine samples taken at various times after the TBI operation. Lectin-specific time-profiles indicate emergence of various glycans in the body fluids at different times after the TBI.
Figure 3:
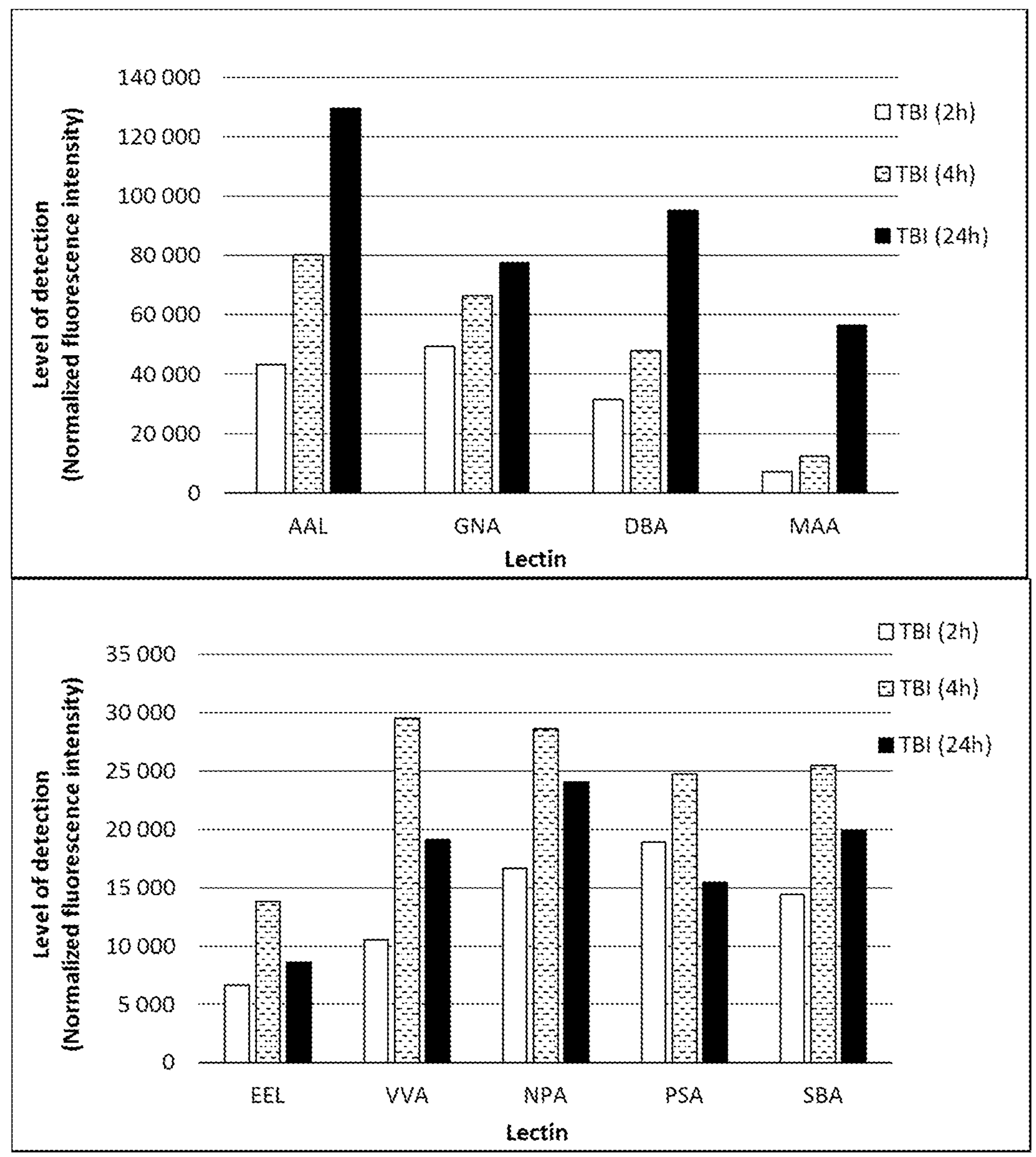
FIG. 3 shows normalized fluorescence intensities of spots of selected lectins contacted with saliva samples taken at various times after the TBI operation. Lectin-specific time-profiles indicate emergence of various glycans in the body fluids at different times after the TBI.

The results summarized in FIGS. 1 to 3 prove that the body fluids of TBI animals contain glycans or glycan-containing complexes showing significantly elevated binding to particular lectins, compared with the fluids of the sham animals. By selecting appropriate lectins, the TBI detection kit can be adjusted to target different post-TBI time windows.

Example 4

In order to verify the findings of animal experiments, human body fluids, such as urine, blood plasma or serum, and CSF, obtained from TBI patients and healthy control subjects are collected and analysed for glycan-based biomarkers using a lectin assay.

It will be obvious to a person skilled in the art that, as technology advances, the inventive concept can be implemented in various ways. The invention and its embodiments are not limited to the examples described above but may vary within the scope of the claims.

The invention claimed is:

1. A method of diagnosing a brain injury in a subject, the method comprising the steps of:

providing a sample of a bodily fluid from a subject suspected of having a brain injury, wherein said sample is a urine sample or a saliva sample;

contacting said sample with a lectin array;

determining the level of glycan in said sample bound to at least one lectin in the lectin array;

comparing the determined level of said glycan bound to at least one lectin to a level of said glycan in a sample from a healthy control;

detecting, in the sample from the subject, an elevated level of the glycan bound to at least one lectin compared to the level in the healthy control, wherein the at least one lectin is selected from the group consisting of *Galanthus nivalis* (GNA), *Allium sativum* (ASA), *Narcissus* pseudo *narcissus* (NPA), *Pisum sativum* (PSA), *Datura stramonium* (DSA), *Leucoagglutinin* (PHA-L), *Sambucus nigra* (SNA-I) and *Hippeastrum hybrid* (HHA);

diagnosing the presence of a brain injury in the subject from the elevated level of the glycan bound to the at least one lectin; and performing at least one neuroimaging procedure selected from the group consisting of x-ray, computerized tomography (CT) scan, and magnetic resonance imaging (MRI) on the subject in whom the elevated level of the glycan is detected and the presence of the brain injury is diagnosed.

2. The method according to claim 1, wherein said brain injury is selected from the group consisting of traumatic brain injury (TBI), mild TBI, severe TBI, or acquired brain injury (ABI).

3. The method according to claim 1, wherein said determining further comprises using mass spectrometry, electrophoresis, a chromatographic method, an enzyme assay, a binding assay, or a combination thereof.

4. The method according to claim 2, wherein said traumatic brain injury is a concussion.

5. The method according to claim 3, wherein said determining further comprises using MALDI-TOF mass spectrometry.

6. The method according to claim 1, wherein said determining further comprises using a reagent selected from the group consisting of a capture reagent, a detection reagent, a secondary detection reagent and a primary detection reagent.

7. The method according to claim 1, wherein said determining is carried out by using a kit comprising at least one lectin that selectively binds to glycan in said sample, and a control for comparing to a measured value of binding.

8. The method according to claim 7, wherein the kit further comprises a detectable label, or a colour, dye, luminescent, or fluorescent agent.

* * * * *